United States Patent [19]

van Vliet

[11] Patent Number: 4,647,707

[45] Date of Patent: Mar. 3, 1987

[54] HYDROFORMYLATION OF OLEFINS

[75] Inventor: Arie van Vliet, Maassluis, Netherlands

[73] Assignee: Exxon Research & Engineering Co., Florham Park, N.J.

[21] Appl. No.: 803,090

[22] Filed: Nov. 27, 1985

[30] Foreign Application Priority Data

Nov. 30, 1984 [GB] United Kingdom ............... 8430226

[51] Int. Cl.$^4$ ............................................. C07C 29/16
[52] U.S. Cl. ...................................... 568/882; 568/913
[58] Field of Search ................................. 568/882, 913

[56] References Cited

U.S. PATENT DOCUMENTS

| | | | |
|---|---|---|---|
| 2,594,341 | 4/1952 | Owen et al. | 568/882 |
| 2,595,096 | 4/1952 | Parker | 260/638 |
| 2,623,074 | 12/1952 | Ratcliff | 568/882 |
| 2,671,118 | 3/1954 | Mertzweiller | 260/638 |
| 2,757,203 | 7/1956 | Hale | 260/604 |
| 2,779,794 | 1/1957 | Catterall | 260/604 |
| 2,779,796 | 1/1957 | Munger | 260/604 |
| 2,905,716 | 9/1959 | Buchner et al. | 260/601 |
| 3,092,670 | 6/1963 | Gwynn et al. | 260/638 |
| 4,048,233 | 9/1977 | Falbe et al. | 260/604 |
| 4,138,588 | 2/1979 | Tummes et al. | 568/882 |
| 4,443,638 | 4/1984 | Yates | 568/882 |

FOREIGN PATENT DOCUMENTS

| | | | |
|---|---|---|---|
| 588627 | 12/1959 | Canada | 568/882 |
| 594124 | 3/1960 | Canada | 568/882 |
| 766243 | 8/1967 | Canada | 568/913 |
| 1411073 | 10/1975 | United Kingdom | |

*Primary Examiner*—J. E. Evans
*Attorney, Agent, or Firm*—J. B. Murray, Jr.

[57] ABSTRACT

The higher alcohol yield of a hydroformylation process including hydroformylation, catalyst removal, hydrogenation and higher alcohol separation stages is improved by subjecting the Heavy Oxo Fraction (HOF) obtained following higher alcohol separation to steam cracking in the presence of a catalyst system comprising a dehydration-catalytic metal on an acidic support. The resultant cracked HOF mixture comprising a major proportion of olefin and saturated hydrocarbon is recycled to the hydroformylation stage.

12 Claims, No Drawings

HYDROFORMYLATION OF OLEFINS

This invention relates to the hydroformylation process, which in general terms is a process involving the preparation of oxygenated organic compounds by the reaction of carbon monoxide and hydrogen (synthesis gas) with carbon compounds containing olefinic unsaturation, and is particularly concerned with the treatment and recycling of by products of the primary oxo-reaction.

The oxo reaction is performed under hydroformylation conditions in the presence of a carbonylation catalyst or catalyst precursor such as dicobaltoctacarbonyl, and results in the formation of a compound e.g. an aldehyde which has one more carbon atom in its molecular structure than the feedstock. Subsequent hydrogenation of the primary product leads to higher alcohols which may be converted into plasticizers.

Typically in higher alcohol production the feedstock for a hydroformylation process is a commercial $C_6$–$C_{12}$ olefin fraction and the desired end product is the respective $C_7$–$C_{13}$ saturated alcohol or derived mixed product, produced by hydrogenation of the aldehyde oxonation product. By virtue of the nature of the feedstock commonly available to industry, and indeed of the catalyst and reaction parameters employed, the hydroformylation reaction inevitably yields a range of products due to the numerous secondary reactions which take place. The main products of the hydroformylation unit are aldehydes and alcohols, with side reactions in the hydroformylation, demetalling and hydrogenation sections of the process system usually producing some 5 to 20 wt. % of high boiling materials such as aldols, esters, ethers and acetals. Such high boiling materials, which represent a serious yield loss to the alcohol producer, are collectively termed the Heavy Oxo Fraction (HOF), and are formed in large part by condensation, esterification and dehydration reactions.

In a conventional higher oxo alcohol process, the feedstock as described above is fed together with synthesis gas into an oxonation unit where catalytic hydroformylation takes place using a catalyst such as cobalt in the form of e.g. dicobaltoctacarbonyl or hydrocobalt carbonyl as the active catalyst species. The oxonation unit product passes to a unit for removing catalyst, and then to a hydrogenation unit where it is hydrogenated to form the desired higher alcohol. The product mixture at this stage, comprising the higher alcohol, the high boiling HOF and a low boiling fraction termed the Light Oxo Fraction (LOF), is then passed to a distillation unit where LOF. HOF and desired alcohol product are physically separated.

The LOF passing off overhead is a low value product, typically containing unreacted olefin feed and paraffins. The HOF, as mentioned usually contains dimers such as ethers, esters, aldols and ether-alcohols (e.g. $C_{20}$ compounds for $C_{10}$ alcohol production) and trimers such as acetals (e.g. $C_{30}$ compounds for $C_{10}$ alcohol production) and heavier; although substantially alcohol free (apart from the heavy aldols and etheralcohols), it may contain a minor amount of alcohol which has not been removed in the distillation stage. Again such HOF is conventionally purged from the system at low value. It is desirable, therefore, to develop a more profitable use of HOF which can readily be incorporated into an oxo process system and which serves to increase the yield of more useful products of such a system.

Some such uses have already been proposed. Thus according to U.S. Pat. No. 4,048,233 (Ruhrchemie AG), HOF termed "thick oil" residue therein) is converted to synthesis gas ($H_2$/CO mixture) by catalytic splitting at high temperatures using defined proportions of water vapour and carbon dioxide and a catalyst containing from 2 to 25 wt. % nickel, optionally on a carrier such as alumina. The splitting takes place at temperatures of from 600° to 900° C. and pressures up to 30 atmospheres, and the synthesis gas product is recycled to the oxonation unit. Indeed the document teaches that after initial start up the synthesis gas product may constitute the sole supply of said gas to the system. There is no teaching though that useful materials other than synthesis gas may be produced from "thick oil" for recycle to the reaction system.

According to GB Pat. No. 1 411 073 (Kuhlmann) the aldehyde yield of an oxo process for producing aldehydes may be improved by a series of treatments which includes at one point hydroysis of so-called heavy products. In the disclosed technique the crude product from the oxo reactor is first distilled to remove unreacted hydrocarbons, and then distilled to separate the desired aldehyde product. The remaining materials, products of secondary reactions in the oxo reactor, are, without any intermediate hydrogenation (which is considered undesirable and complicated according to page 1 lines 39–50 of the disclosure) then subjected to a further distillation to remove alcohols and formates. Following such removal the alcohol/formate distillate is catalytically dehydrogenated and returned to the hydroformylation outlet of the system. It is noted that Kuhlmann employs conventional dehydrogenation catalysts, eg copper/zinc, and gives no teaching to employ a steam medium at this stage. The residual heavy products are catalytically steam hydrolysed at atmospheric pressure, 250°–400° C., and a preferred 1:1 w/w steam ratio to form a mixture of alcohols, aldehydes and residual heavy products, such mixture being recycled to the hydroformylation output after removal of the residual heavy products.

It is noted here that the Kuhlmann method employs no hydrogenation stage; and furthermore that the nature of the secondary reaction products is considerably changed by incorporation of a hydrogenation step into the system. In particular the aldehyde content of the stream is minimised and of course, following hydrogenation there are no formates present in the stream, which formates are necessarily removed prior to hydrolysis in accordance with Kuhlmann.

U.S. Pat. No. 2,757,203 (Hale) also addresses the question of the secondary reactions occuring in the oxo process and in particular identifies that acetals may be formed, thus reducing the aldehyde/alcohol yield. Recognising that acetal formation is acid catalysed, Hale makes use of the equilibrium nature of the reaction by hydrolysing the acetal containing crude product, optionally after hydrogenation, in the presence of aqueous mineral acid at 212°–400° F. whilst simultaneously continuously distilling off the aldehyde. Hale provides no teaching to catalyse the hydrolysis with other than a mineral acid, nor does he propose performing the reaction on the heavy products obtained following removal of alcohol from the crude oxo product.

U.S. Pat. No. 2,779,794 (Catterall) teaches the heat soaking of the crude oxo product in contact with water in order to decompose cobalt catalyst compounds contained therein to an aqueous slurry, but the aim is simply catalyst removal, not any modification of the organic phase. Furthermore, there is no suggestion that catalytic steam hydrolysis might be used in the technique taught.

U.S. Pat. No. 2,905,716 (Buchner et al) teaches the removal of metal and acetals from a crude aldehyde containing oxo product by contacting the stream with water at 150°–200° C. in an elongate, unfilled reactor at elevated pressure, but makes no suggestion to use catalytic techniques nor any indication to recycle the resulting product.

U.S. Pat. No. 3,092,670 (Gwynn et al) teaches the removal of unreacted olefin from the crude oxo product by fractionating the demetalled product in the presence of steam. Subsequently the remaining material, containing polymeric secondary reaction products, is subjected to conventional hydrogenation to yield the desired alcohol product.

U.S. Pat. No. 2,779,796 (Munger) is also concerned with the removal of cobalt from crude oxo product streams and teaches the injection of live steam at 212°–400° F. into the crude product to achieve this objective. During such treatment all the heat required is supplied by the live steam and the crude product is not allowed to come into contact with any fixed heating surface having a temperature greater than the water/product mixture boiling point.

U.S. Pat. No. 2,595,096 (Parker) seeks to improve the alcohol yield of the oxo process by treating the bottoms obtained following oxonation, hydrogenation and removal of, first, unreacted hydrocarbons and then alcohols from the hydrogenated product stream. Such bottoms are said to contain polymerised aldehydes and ketones, high molecular weight ethers and secondary alcohols and polymerised hydrocarbons, principally acetals. The acetal content of the bottoms is hydrolysed with dilute mineral acid, with water (steam) or by other catalytic means to form quantities of alcohols and aldehydes which may themselves by recycled to the hydrogenation stage. Making specific reference to Parker, the process is described at column 5 lines 33–65 with reference to the drawing. Thus the acetal content of the bottoms derived from oxonating a $C_7$ olefin is hydrolysed at 200°–250° F. (91°–121° C.) using 10% aqueous hydrochloric acid solution, although (column 5 line 68-column 6 line 2) there is also disclosure of the possible use of live steam at 300°–400° F. (149°–204° C.). Furthermore, alternatives to dilute mineral acids for the conversion of acetals in the bottoms to aldehydes and alcohols are stated at column 6 lines 23–27 to be other catalytic agents such as alumina, silica and metals or metal oxide of the eighth group of the periodic system. Example I of Parker specifically shows hydrolysis of the bottoms derived from $C_7$ olefin oxonation with an equal volume of water in an autoclave at 350° F. (175° C.), giving an overall alcohol yield increase of 2–3%. Example II takes the same bottoms and, following removal of residual $C_8$ alcohol, hydrolyses them with water alone (steam at 175° C.) and with 10% HCl solution at 220° F. (102°C.) to convert the acetal content to alcohol and aldehyde. Such relatively mild hydrolysis conditions may be acceptable and useful for improving the alcohol yield of systems which contain bottoms fractions having relatively large proportions of the acetals, but the economic climate of present day higher alcohol production is much worse than in 1949, the date of Parker. There is a greater desideratum to maximise yields of higher alcohol, and heavy bottom products are not readily consigned for fuel use. There is a need therefore for a method which can improve alcohol yield of the oxo process virtually regardless of the nature of the secondary products which may be present in the crude oxo product stream, that is to say even in cases where the acetal content of such crude product streams after hydrogenation is relatively small.

Moreover, it is noted that there is no teaching in Parker towards yield improvement by a route which maximises olefin yield by further catalytic steam treatment of the heavy products and theeafter improves alcohol yield by recycle of the resulting olefin rich fraction to the hydroformylation stage.

Thus according to the present invention there is provided a process for producing a higher alcohol from an olefinic feedstock by hydroformylating the feedstock with synthesis gas in the presence of a hydroformylation catalyst to form a product mixture containing higher aldehyde, alcohol, unreacted feed and secondary products; removing catalyst therefrom; hydrogenating the substantially catalyst free mixture to convert the aldehyde to higher alcohol; distilling the higher alcohol-containing product mixture to separate the higher alcohol from a lower boiling Light Oxo Fraction (LOF) and a higher boiling Heavy Oxo Fraction (HOF); subjecting the HOF to catalytic steam cracking using as catalyst system a dehydrationcatalytic metal on an acidic support, to form HOF residue and a cracked HOF mixture comprising a major proportion of olefin and saturated hydrocarbon, and a minor proportion of higher alcohol and higher aldehyde; and recycling the cracked HOF mixture to the hydroformylation stage of the process.

The hydroformylation conditions employed to produce the crude product mixture may be those which are well known in the art. For example the hydroformylation reaction may be carried out at a pressure of 150–300 atm and a temperature of from 125°–175° C. The hydroformylation catalyst used may be for example cobalt in desired active form, preferably in a concentration of from 0.05–3 wt. % based on the olefinic feed. Typically the syn gas used might have a $H_2$:CO volume ratio in the range 0.9:1–1.5:1.

Preferably the catalytic steam cracking of the HOF is performed at temperatures in the range 240°–350° C., more preferably 250°–300° C., in order to maximise the proportion of olefinic components in the resulting cracked HOF mixture.

As examples of catalysts which may be used in order to promote the reactions leading to the desired steam cracking of the HOF, nickel may be particularly mentioned as being catalytically active. The acid supports on which the metal is carried may be for example alumina and/or silica. A catalyst which has been found to be effective in accordance with the invention is nickel carried on an alumina/silica support, such as Ni 5124T, a product of Harshaw, although other suitable supported metals may be employed. Without wishing to be bound by theory, it is believed that the acidic support may serve to catalyse hydrolysis/dehydration reactions, and the metal to catalyse dehydration reactions, the combination thus yielding the desired high proportion of unsaturated hydrocarbons in the cracked HOF mixture. Other catalyst systems which may be mentioned comprise for example an aluminium oxide and/or silicon oxide support having for example Co or Cr as the metals in the active sites.

The pressure at which the HOF steam cracking step is performed is preferably in the range of from 100 to 1000 kPa (1-10 bar), more preferably 1-3 atm abs. It is preferred that the cracking of the HOF is performed with the weight ratio of steam and HOF in the range 0.1:1 to 2:1, more preferably 0.2:1 to 1.2:1. For economic reasons the optimum range has been found to be from 0.4:1 to 1.2:1.

The use of the defined catalyst system to crack the HOF to a mixture rich in olefins enables the oxo-process operator to improve overall alcohol yield following the recycle stage, since it introduces into the hydroformylation stage olefins which would otherwise be lost to the system as HOF. For example with a nickel on alumina catalyst it may be possible to obtain HOF residue and a cracked HOF mixture of some 10% alcohol/aldehyde and some 90% olefin/paraffin. In general it has been found that for the use of the same catalyst, with increase in steam cracking temperatures there is a higher conversion and higher selectivity to olefin, although of course at the higher temperature ranges account must be taken of the economics of the process and the tendency to produce undesired by-products.

The steam cracking of the HOF in accordance with the invention yields as well as the cracked HOF mixture, a HOF residue which is typically oxygenated dimers and trimers ($C_{20}$ to $C_{30}+$ materials for a $C_{10}$ alcohol).

Unless the cracked HOF mixture is automatically separated from the HOF residue during the steam cracking step by virtue of the particular cracking technique employed, the HOF residue should be removed in a subsequent stage (preferably steam or flash distillation) prior to recycle of the cracked HOF mixture. It is particularly preferred that any water remaining in the cracked HOF mixture after cracking should be removed before recycling in order to avoid incidental problems in other stages of the process, for example catalyst deterioration in the hydrogenation unit.

The cracked HOF mixture produced in the HOF steam cracking stage contains olefinic hydrocarbons, paraffins and a minor proportion of higher aldehydes/higher alcohols, and on recycle to the hydroformylation stage the olefinic hydrocarbons are oxonated and upgraded to the higher aldehyde-alcohol. Such higher aldehyde is reduced to desired higher alcohol at the subsequent hydrogenation stage and the overal higher alcohol yield of the process is increased. The saturated hydrocarbons pass through the entire system unreacted, being substantially removed (together with unreacted olefins) as LOF at the distillation stage.

The aldehyde/alcohol content of the recycled cracked HOF mixture passes through the oxonation unit mainly unconverted but some dimers or heavier products may be formed, representing a potential yield loss. In the downstream hydrogenation unit the aldehyde is reduced to the desired higher alcohol. It is therefore desirable to adopt cracking conditions such that the proportion of aldehydes/alcohol in the cracked HOF mixture is minimised, since the greater the aldehyde/alcohol content of the recycle mixture, the higher is the yield loss through oligomerisation in the hydro formylation unit.

Repeated performance of the process according to the invention has shown that the HOF typically has a composition comprising 0-5 wt. % alcohols, 15-25 wt. % ethers, 45-65 wt. % ether-alcohols 2-10 wt. % esters, and 5-25 wt. % acetals, with possibly extremely minor amounts of other material eg up to 2 wt. % heavier depending on feedstock and selected process conditions. Depending on the feed to the oxo reactor, such HOF is typically the material boiling in the range 200°-450° C. at atmospheric pressure. The HOF residue produced after cracking typically comprises a major amount of heavy oxygenated compounds such as ethers, etheralcohols, esters and acetals, and minor amounts of lighter alcohol/aldehyde/olefin/paraffin components. Again depending on the oxo-feed, such HOF residue typically boils at temperatures above 200°-230° C. at atmospheric pressure, although as will be understood, the attribution of a specific boiling temperature to a complex mixture of components is not easy, depending amongst other things on whether distillation is on a continuous or batch basis, the length of the distillation column and the point or phase in the column at which temperature is measured. The cracked HOF mixture will typically comprise less than 30 wt. % alcohol/aldehyde, less than 10 wt. % HOF residue, and the balance olefin/saturated hydrocarbon; the amounts of these components will depend on the temperature selected for separation, which will of course depend on the carbon numbers of the feedstock and the degree of separation required by the operator. The boundary between the cracked HOF mixture and the HOF residue depends to an extent on the wishes of the process operator and the economics of his particular oxo-process. It is generally the case that the HOF residue comprises substantially the dimer and trimer and even heavier components of the organic phase produced by cracking the HOF under the specified conditions. Preferably the mixture which is recycled to the hydroformylation stage of the process is the one which is substantially the monomer components of the cracked HOF organic phase, that is those compounds containing one more carbon atom in their molecules than the carbon number of the feedstock to the overall process. Preferably the cracked HOF mixture will contain no more than about 10 wt. % of dimers and above, whilst the residue preferably contains less than 10 wt. % of light monomeric components.

It is preferred that the mixture as recycled should contain olefin/paraffin in amounts which correspond to greater than about 50 wt. % of the organic material obtained following cracking of the HOF since this helps to maximise the overall process yield of higher alcohol. With regard to the cracked HOF mixture as recycled in accordance with the invention, this should contain a major proportion of olefin/paraffin components based on the total of alcohol/aldehyde components plus olefin/paraffin components. On this basis, the mixture contains a maximised amount of olefin/paraffin, for example from 70-98 wt. %, more preferably 80-95 wt. % and especially 85-92 wt. % of the olefin/paraffin component. Of course it is preferred that the amount of unsaturated hydrocarbons in this component is minimised.

The process according to the invention is particularly suitable for use with branched olefin feedstocks, preferably these with carbon numbers $C_6$-$C_{12}$, more preferably $C_8$-$C_{10}$ and results in improved yields of branched higher alcohol, and also in by-products having higher value.

The following examples illustrate the invention.

EXAMPLE 1

(1) Hydroformylation Stage

Hydroformylation was performed using a feed comprising (i) syn gas containing hydrogen and carbon monoxide in a molar ratio of 1.16:1 and (ii) a commercially available stream of branched nonenes including also about 2 wt % octenes and about 8 wt % decenes. The olefin feed was delivered at a rate of 1.5 l/hr (1115 g/hr), and the syn gas at a rate of 640 standard l/hr, into three 1.0 liter capacity oxonation reactors arranged in series, and the reaction was carried out at a pressure of 300 atm and a temperature of 175° C., using a cobalt catalyst at 0.3 wt % based on the feed.

(2) Decobalting Stage

The crude oxo product containing higher aldehyde, resulting from stage (1) was decobalted to less than 10 ppm cobalt in conventional manner by neutralizing the cobalt hydrocarbonyl with sodium hydroxide and washing with water.

(3) Hydrogenation Stage

The product of stage (2) was fed to a conventional hydrogenation train where, using Cu/Cr and Ni catalysts, a hydrogen pressure of 50 bars and a temperature of 120°-170° C., the product containing higher aldehydes, formates and acetals was converted to a hydrogenation product mixture containing the desired higher alcohol.

(4) Separation Stage

The mixture of stage (3) was then distilled under vacuum to produce three fractions, a light oxo fraction (LOF), a heavy oxo fraction (HOF) and a higher alcohol fraction (HA) as shown in Table 1.

TABLE 1

| Fraction | Amount | Alcohol content | Boiling Range |
|---|---|---|---|
| LOF | 165 g/hr | ≦0.5 wt % | 125–187° C. |
| HA | 1003 g/hr | | 187–225° C. |
| HOF | 207 g/hr | ≦3 wt % | >225° C. |

The yield of HA (chiefly $C_{10}$ alcohols with minor amounts of $C_9$ and $C_{11}$ alcohols) corresponded to 89.9 g per 100 g of feed olefin.

(5) HOF Cracking Stage

The HOF product separated in stage (4) was introduced in upflow manner and in admixture with an equal weight of steam into a steam cracking reactor. The reactor contained Harshaw Ni 5124 T supported nickel catalyst and operated at 280° C. and a pressure of 1.3 atm. The flow of HOF/steam through the reactor was such as to corespond to a space velocity of 0.5 v/v/hr expressed as volume of HOF per volume of catalyst per hour. After cracking, the cracked product was subjected to flashing at 200° C. to produce an overhead stream comprising cracked HOF mixture and water (steam), and a bottoms stream of HOF residue. After condensation of the overheads, the water was separated from the cracked HOF mixture. Under atmospheric flashing conditions it is difficult to attribute single temperatures to the streams obtained, but principally the HOF residue was the fraction boiling above 230° C. and comprised a major proportion of oxygenated compounds of carbon number $C_{18}$–$C_{30}$ (predominantly $C_{18}$–$C_{22}$) with some even heavier products, and a minor proportion of alcohol/aldehyde/olefin components. The cracked HOF mixture was substantially the fraction separating below 220° C. and comprised a small proportion of HOF residue, together with larger amounts of an olefin fraction, generally $C_8$–$C_{11}$ olefins with predominantly $C_{10}$ olefin and a very low level of saturated hydrocarbon, and a minor proportion of an alcohol/aldehyde mixed fraction with carbon numbers $C_9$–$C_{11}$, predominantly $C_{10}$.

The compositions of cracked HOF mixture and HOF residue are shown in Table 2.

TABLE 2

| | Composition (wt %) |
|---|---|
| Cracked HOF mixture (145 g/hr) | |
| olefin/saturated hydrocarbon | 69.4 |
| alcohol/aldehyde | 25.7 |
| HOF residue | 4.9 |
| HOF residue (62 g/hr) | |
| alcohol/aldehyde/olefin | 5 |
| HOF residue | 95 |

(6) Recycle Stage

The cracked HOF mixture produced and separated in the preceding stage at a rate of 145 g/hr was delivered together with 1.5 l/hr (1115 g/hr) of the same nonene feed used previously and 740 l/hr syn gas to the hydroformylation stage (1) and the process was repeated, but effectively with recycle of cracked HOF mixture. Distillation of the hydrogenation stage product, in stage (4), yielded the same three fractions as previously without recycle, as shown in Table 3.

TABLE 3

| Fraction | Amount | Alcohol content | Boiling Range |
|---|---|---|---|
| LOF | 186 g/hr | ≦0.5 wt % | 125–187° C. |
| HA | 1135 g/hr | | 187–235° C. |
| HOF | 231 g/hr | | >235° C. |

The LOF, in addition to a very small amount of alcohol, contained unreacted olefins and paraffins of the same carbon number as the feed.

It will be seen from the above that the process wherein the HOF produced is cracked in accordance with the invention, and the cracked HOF mixture is recycled to the hydroformylation stage, resulted in an overall yield of higher alcohol which was 101.79 g per 100 g olefin feed input, an improvement of about 13% over the process where no HOF cracking and recycle took place.

EXAMPLE 2 (Comparison)

The procedure of Example 1 was substantially repeated, with the exception that the HOF produced was 'cracked' in a reactor filled with distillation column packing (inert stainless steel balls) instead of the catalyst system specified in accordance with the invention. The cracked product, after removal of water, was found to have only a minimal content of olefinic products, such that recycle of such product to the oxonation reactor gave no measurable increase in the overall process yield of desired higher alcohol.

I claim:

1. A process for producing higher alcohols from an olefinic feedstock which comprises: (a) hydroformylating said olefinic feedstock with synthesis gas in the presence of a hydroformylation catalyst to form a hydroformylation product mixture containing higher aldehydes and higher alcohols having a carbon number which is one carbon atom greater than said olefinic feedstock, unreacted olefinic feedstock and secondary reaction products; (b) treating said hydroformylation product mixture to remove said hydroformylation catalyst therefrom and to form a substantially catalyst-free hydroformylation product mixture; (c) hydrogenating said substantially catalyst free hydroformylation product mixture to convert said higher aldehydes to additional amounts of said higher alcohols; (d) distilling the higher alcohol-containing hydrogenation product mixture formed in step (c) to separate (i) a lower boiling light oxo fraction and (ii) said higher alcohols from (iii) a higher boiling heavy oxo fraction; (e) recovering said alcohols as product and subjecting the heavy oxo fraction to catalytic steam cracking at a temperature of from 240° to 350° C. in the presence of a cracking catalyst comprising a dehydration-catalytic metal on an acidic support, to form heavy oxo fraction residue and a cracked heavy oxo fraction mixture comprising a major proportion of olefin and saturated hydrocarbon and a minor proportion of higher alcohol and higher aldehyde; and (f) recycling said cracked heavy oxo fraction mixture to the hydroformylation stage of the process.

2. A process according to claim 1 wherein said dehydration-catalytic metal comprises nickel.

3. A process according to claim 1 wherein said acidic support comprises a member selected from the group consisting of alumina, silica and mixtures thereof.

4. A process according to claim 1, wherein said steam cracking catalyst comprises nickel on an alumina/silica support.

5. A process according to claim 1 wherein said steam cracking of the heavy oxo fraction is performed using steam and heavy oxo fraction at a weight ratio in the range 0.1:1–2:1.

6. a process according to claim 5 wherein said steam: heavy oxo fraction weight ratio is in the range 0.2:1–1.2:1.

7. A process according to claim 5 wherein said steam cracking is performed using steam and heavy oxo fraction at a weight ratio in the range 0.4:1–1.2:1.

8. A process according to claim 1 wherein said steam cracking is performed at a temperature of 250°–300° C.

9. A process according to claim 1 wherein said catalytic steam cracking of the heavy oxo fraction is performed at a total pressure of 1–10 bar abs.

10. A process according to claim 9 wherein said catalytic steam cracking of the heavy oxo fraction is performed at a total pressure of 1–3 atm abs.

11. A process for producing higher alcohols from an olefinic feedstock comprising olefins containing from 6 to 12 carbon atoms which comprises: (a) hydroformylating said olefinic feedstock with synthesis gas in the presence of a hydroformylation catalyst to form a hydroformylation product mixture containing higher aldehydes and higher alcohols having a carbon number which is one carbon atom greater than said olefinic feedstock, unreacted olefinic feedstock and secondary reaction products; (b) treating said hydroformylation product mixture to remove said hydroformylation catalyst therefrom and to form a substantially catalyst-free hydroformylation product mixture; (c) hydrogenating said substantially catalyst-free hydroformylation product mixture to convert said higher aldehydes to additional amounts of said higher alcohols; (d) distilling the higher alcohol-containing hydrogenation product mixture formed in step (c) to separate (i) a lower boiling light oxo fraction and (ii) said higher alcohols from (iii) a higher boiling heavy oxo fraction; (e) recovering said alcohols as product and subjecting the heavy oxo fraction to catalytic steam cracking at a temperature of from 240° to 350° C. in the presence of a cracking catalyst comprising a dehydration-catalytic metal on an acidic support, to form heavy oxo fraction residue comprising dimeric and heavier components based on said higher alcohol carbon number and no more than 10 wt % of monomeric components, and a cracked heavy oxo fraction mixture comprising monomeric components based on said higher alcohol carbon number and no more than 10 wt % of dimeric and heavier components and containing a major proportion of olefin and saturated hydrocarbon, and a minor proportion of higher alcohol and higher aldehyde; and (f) recycling said cracked heavy oxo fraction mixture to the hydroformylation stage of the process.

12. A process according to claim 11 wherein said hydroformylation catalyst comprises a cobalt-containing hydroformylation catalyst and wherein said catalytic steam cracking is performed at a total pressure of from 1 to 3 atms abs and employing a steam:heavy oxo fraction weight ratio in the range of 0.4:1 to 1.2:1.

* * * * *